United States Patent
Bell et al.

(10) Patent No.: US 9,458,085 B2
(45) Date of Patent: Oct. 4, 2016

(54) FORMULATIONS

(75) Inventors: Gordon Alastair Bell, Bracknell (GB); Jeffrey Steven Wailes, Bracknell (GB); Anne Waller, Bracknell (GB); John Henry Nettleton-Hammond, legal representative, Bracknell (GB)

(73) Assignee: Syngenta Limited, Guildford Surrey (GB)

( * ) Notice: Subject to any disclaimer, the term of this patent is extended or adjusted under 35 U.S.C. 154(b) by 0 days.

(21) Appl. No.: 13/812,231

(22) PCT Filed: Jul. 27, 2011

(86) PCT No.: PCT/IB2011/053339
§ 371 (c)(1),
(2), (4) Date: Mar. 24, 2014

(87) PCT Pub. No.: WO2012/014162
PCT Pub. Date: Feb. 2, 2012

(65) Prior Publication Data
US 2014/0249328 A1    Sep. 4, 2014

(30) Foreign Application Priority Data
Jul. 27, 2010 (GB) .................................. 1012587.0

(51) Int. Cl.
| | | |
|---|---|---|
| A01N 25/02 | (2006.01) |
| C07C 69/60 | (2006.01) |
| A01N 37/06 | (2006.01) |
| C07C 69/65 | (2006.01) |
| C07C 317/22 | (2006.01) |
| C07C 69/618 | (2006.01) |

(52) U.S. Cl.
CPC ............... *C07C 69/60* (2013.01); *A01N 25/02* (2013.01); *A01N 37/06* (2013.01); *C07C 69/618* (2013.01); *C07C 69/65* (2013.01); *C07C 317/22* (2013.01)

(58) Field of Classification Search
CPC ....... C07C 69/60; A01N 25/02; A01N 37/06
USPC .......................................... 560/190; 424/405
See application file for complete search history.

(56) References Cited

FOREIGN PATENT DOCUMENTS

| | | | |
|---|---|---|---|
| CN | 122186 | 5/1996 | |
| JP | 8175909 | 7/1996 | |
| JP | 2006232709 | * 9/2006 | |
| WO | WO 2010/094408 | * 2/2010 | ............. A01N 25/02 |
| ZA | 8906171 | 8/1989 | |

OTHER PUBLICATIONS

Caplus Accession No. 1991:96834; abstract of Bishop, Richard Timothy, "Sustained-release agricultural chemicals with polymer coating," 1990.*
CAS Registry No. 105-76-0, entered Nov. 16, 1984.*
International Search Report, International Application No. PCT/IB2011/053339, completion date: Nov. 25, 2011.

* cited by examiner

*Primary Examiner* — Kamal Saeed
*Assistant Examiner* — Janet L Coppins
(74) *Attorney, Agent, or Firm* — James Cueva

(57) ABSTRACT

This invention relates to a formulation comprising a compound of formula (I) where R1 and R2 are each independently hydrogen, optionally substituted C1-18 alkyl, optionally substituted C1-18 alkenyl, optionally substituted C3-8 cycloalkyl, optionally substituted C3-8 cycloalkenyl or optionally substituted aryl; provided that the total number of carbon atoms in R1 and R2 is an integer from 5 to 40 inclusive; the use of a compound of formula (I) (i) as an adjuvant provided that the total number of carbon atoms in R1 and R2 is an integer from 5 to 40 inclusive; and (ii) as a solvent provided that the total number of carbon atoms in R1 and R2 is an integer from 5 to 20 inclusive; to certain novel compounds of formula (I) and to a process for preparing those novel compounds.

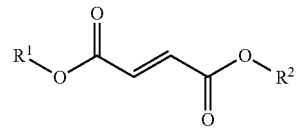

17 Claims, No Drawings

FORMULATIONS

This application is a 371 of International Application No. PCT/IP2011/053339 filed Jul. 27, 2011, which claims priority to GB 1012587.0 filed Jul. 27, 2010 the contents of which are incorporated herein by reference.

This invention relates to the use of certain fumarate compounds as solvents, especially in formulations, particularly in agrochemical formulations and in environmentally friendly formulations; and to certain novel compounds. The solvents of the present invention are found to be particularly effective at forming stable emulsions in water.

Nowadays, the Formulation Chemist is required to address a number of environmental criteria when developing new formulations. Ideally, a suitable solvent will display many or all of the following properties: a low water solubility; an excellent dissolving power for pesticides or other organic molecules; made from plant or animal renewable resources; low skin irritation; low ecotoxicity, for example to daphnia; low volatile organic content; and a high flash point. The compounds of the present invention each display all or many of these properties, in particular they form stable emulsions in water; the compounds may be used effectively as solvents.

Accordingly, the present invention provides the use of a compound of formula (I) as a solvent

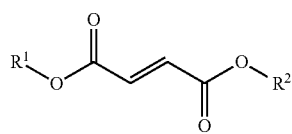

(I)

where $R^1$ and $R^2$ are each independently hydrogen, optionally substituted [i.e. substituted or unsubstituted] $C_{1-18}$ alkyl, optionally substituted [i.e. substituted or unsubstituted] $C_{1-18}$ alkenyl, optionally substituted [i.e. substituted or unsubstituted] $C_{3-8}$ cycloalkyl, optionally substituted [i.e. substituted or unsubstituted] $C_{3-8}$ cycloalkenyl or optionally substituted [i.e. substituted or unsubstituted] aryl; provided that the total number of carbon atoms in $R^1$ and $R^2$ is an integer from 5 to 40 inclusive, suitably from 5 to 20 inclusive. The expression "the total number of carbon atoms in $R^1$ and $R^2$ is an integer from 5 to 20 inclusive" means, for example, that if $R^1$ contains 2 carbon atoms, then $R^2$ may contain from 3 to 18 carbon atoms.

The present invention also relates to fumarates which can act as an adjuvant to enhance significantly the biological performance of a pesticide.

Accordingly, the present invention provides the use as an adjuvant of a compound of formula (I) as defined above; suitably it provides the use as an adjuvant of a compound of formula (I)

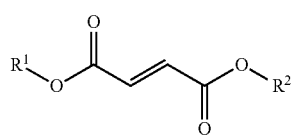

(I)

where $R^1$ and $R^2$ are each independently hydrogen, optionally substituted $C_{1-18}$alkyl, optionally substituted $C_{1-18}$alkenyl, optionally substituted $C_{3-8}$ cycloalkyl or optionally substituted $C_{3-8}$ cycloalkenyl; provided that the total number of carbon atoms in $R^1$ and $R^2$ is an integer from 5 to 40 inclusive [suitably from 5 to 20 inclusive].

Alkyl groups and moieties are straight or branched chains. Examples are methyl, ethyl, iso-propyl, n-propyl, n-butyl, sec-butyl, tert-butyl, n-amyl, iso-amyl [3-methylbutyl], n-pentyl and n-nexyl.

Alkenyl groups and moieties may be in the form of straight or branched chains and, where appropriate, may be of either the (E)- or (Z)-configuration. Examples are vinyl and allyl.

Cycloalkyl includes cyclyopropyl, cyclobutyl and cyclopentyl.

Cycloalkenyl includes cyclobutenyl and cyclopentenyl.

Aryl includes phenyl. Suitably aryl is phenyl.

Optional substituents on alkyl are selected from hydroxy, =O, halo, —NH$_2$, —C(=O)NH$_2$, —C(=O)OH, —O(C$_{1-3}$)alkyl and C$_{1-3}$ cycloalkyl; suitably they are selected from hydroxyl and halo.

Optional substituents on alkenyl are selected from hydroxy, =O, halo, —NH$_2$, —C(=O)NH$_2$, —C(=O)OH, —O(C$_{1-3}$)alkyl and C$_{1-3}$ cycloalkyl; suitably they are selected from hydroxyl and halo.

Optional substituents on cycloalkyl are selected from hydroxy, =O, halo and C$_{1-3}$ alkyl; suitably they are selected from hydroxyl and halo.

Optional substituents on cycloalkenyl are selected from hydroxy, =O, halo and C$_{1-3}$ alkyl; suitably they are selected from hydroxyl and halo.

Optional substituents on aryl are independently selected from C$_{1-3}$ alkyl, halo, cyano, C$_{1-3}$ haloalkyl, C$_{1-3}$ alkoxy, C$_{1-3}$ haloalkoxy, C$_{2-3}$ alkenyl, C$_{1-3}$ alkoxyC$_{1-3}$ alkylene, C$_{1-3}$ alkoxyC(=O)— and C$_{1-3}$ alkylsulphonyl; suitably C$_{1-2}$ alkyl; more suitably methyl.

Suitably optionally substituted aryl is suitably optionally substituted [i.e. substituted or unsubstituted] phenyl or optionally substituted [i.e. substituted or unsubstituted] tolyl; more suitably phenyl or tolyl; preferably phenyl. In one aspect it is optionally substituted phenyl.

Suitably halo is chloro, fluro or bromo; more suitably chloro or fluoro. Suitably $R^1$ is hydrogen or $C_{1-18}$ alkyl optionally substituted by one, two or three hydroxyl groups.

Suitably $R^2$ is $C_{3-18}$ alkyl optionally substituted by one, two or three hydroxyl groups.

Suitably $R^1$ is hydrogen, methyl, ethyl, linear or branched propyl, or linear or branched butyl; more suitably $R^1$ is either propyl or butyl where $R^2$ is either propyl or butyl Suitably $R^2$ is propyl or butyl when $R^1$ is butyl.

Suitably $R^1$ is butyl when $R^2$ is also butyl; more suitably, both are n-butyl.

In one aspect of the present invention, suitably $R^1$ is hydrogen or $C_{1-2}$ alkyl and $R^2$ is substituted or unsubstituted phenyl; suitably $R^1$ is ethyl; suitably $R^2$ is substituted phenyl.

The present invention encompasses all isomers, or mixtures of isomers, of compounds of formula (I) and also encompasses mixtures of two or more different compounds of formula (I).

The selection of solvents for an (agricultural) emulsion concentrate or water-dispersed emulsion formulation is complicated. Often there is a requirement for two different solvents. A solvent which has an aqueous solubility of at least 0.1% w/w [at the relevant temperature] may dissolve appreciably in an agrochemical spray tank full of water, under normal dilution or dispersion conditions [for example, at temperatures of from just above freezing to 35° C.]. Such a solvent will not form stable emulsions in water when formulated with surfactants however it may be an effective solvent for dissolving pesticides. Such a solvent is normally also formulated with an oil of much lower water solubility. Solvents which have aqueous solubility values below 0.1% w/w [at the relevant temperature] are used along with a solvent with the above higher aqueous solubility in order to be able to prepare stable emulsions. The solvent with the low water solubility is normally a poor solvent for dissolving pesticides. The surprising finding about the fumarate solvents of the present invention is that they have a low water solubility yet they are also good solvents for pesticides. This fact is amply displayed in the data given in the Examples.

Table 1 provides structures of suitable compounds of formula (I).

TABLE 1

| Compound Number | $R^1$ | $R^2$ |
|---|---|---|
| 1.1 | $CH_3CH_2CH_2$ | $CH_3CH_2CH_2$ |
| 1.2 | $(CH_3)_2CH$ | $(CH_3)_2CH$ |
| 1.3 | $CH_3CH_2CH_2CH_2$ | $CH_3CH_2CH_2CH_2$ |
| 1.4 | $(CH_3)_2CHCH_2$ | $(CH_3)_2CHCH_2$ |
| 1.5 | $CH_3CH_2CH_2CH_2CH_2$ | $CH_3CH_2CH_2CH_2CH_2$ |
| 1.6 | $CH_3CH_2CH_2CH(OH)CH_2$ | $CH_3CH_2CH_2CH(OH)CH_2$ |
| 1.7 | $CH_3CH(CH_3)CH_2CH_2$ | $CH_3CH(CH_3)CH_2CH_2$ |
| 1.8 | $CH_3CH_2CH_2CH_2CH_2CH_2$ | $CH_3CH_2CH_2CH_2CH_2CH_2$ |
| 1.9 | $CH_3CH_2CH_2CH(CH_3)C(OH)$ | $CH_3CH_2CH_2CH(CH_3)C(OH)$ |
| 1.10 | $CH_3CH_2CH(CH_3)CH_2C(OH)$ | $CH_3CH_2CH(CH_3)CH_2C(OH)$ |
| 1.11 | $CH_3CH(CH_3)CH_2CH_2C(OH)$ | $CH_3CH(CH_3)CH_2CH_2C(OH)$ |
| 1.12 | $HOCH_2CH_2CH_2$ | $CH_3CH_2CH_2$ |
| 1.13 | $ClCH_2CH_2CH_2$ | $CH_3CH_2CH_2$ |
| 1.14 | $CH_2=CHCH_2$ | $CH_3CH_2CH_2$ |
| 1.15 | $CH_3CH_2CH_2$ | $CH_3CH_2$ |
| 1.16 | $CH_2=CHCH_2$ | $CH_3CH_2$ |
| 1.17 | $(CH_3)_2CH$ | $CH_3CH_2$ |
| 1.18 | $CH_3C=CH_2$ | $(CH_3)_2CH$ |
| 1.19 | $CH_3CHCH_2Cl$ | $(CH_3)_2CH$ |
| 1.20 | $CH_3CH_2CH_2CH_2$ | $CH_3$ |
| 1.21 | $CH_3CH_2CH_2CH_2$ | $CH_3CH_2$ |
| 1.22 | $CH_2=CHCH_2CH_2$ | $CH_3CH_2CH_2CH_2$ |
| 1.23 | $ClCH_2CH_2CH_2CH_2$ | $CH_3CH_2CH_2CH_2$ |
| 1.24 | $(CH_3)_2CHCH_2$ | $CH_3$ |
| 1.25 | $(CH_3)_2CHCH_2$ | $CH_3CH_2$ |
| 1.26 | $CH_3CH(=CH_2)CH_2$ | $(CH_3)_2CHCH_2$ |
| 1.27 | $CH_3C(=CH_2)CH_2$ | $(CH_3)_2CHCH_2$ |
| 1.28 | $ClCH_2CH(CH_3)CH_2$ | $(CH_3)_2CHCH_2$ |
| 1.29 | $CH_3CH_2CH_2CH_2CH_2$ | H |
| 1.30 | $CH_3CH_2CH_2CH_2CH_2$ | $CH_3$ |
| 1.31 | $CH_3CH_2CH_2CH_2CH_2$ | $CH_3CH_2$ |
| 1.32 | $CH_3CH_2CH_2CH_2CH_2$ | $CH_3CH_2CH_2$ |
| 1.33 | $CH_3CH_2CH_2CH_2CH_2$ | $CH_3CH_2CH_2CH_2$ |
| 1.34 | $CH_2=CHCH_2CH_2CH_2$ | $CH_3$ |
| 1.35 | $CH_3CH_2CH_2CH_2CH_2CH_2$ | H |
| 1.36 | $CH_3CH_2CH_2CH_2CH_2CH_2$ | $CH_3CH_2$ |
| 1.37 | $CH_2=CHCH_2CH_2CH_2CH_2$ | $CH_3CH_2CH_2$ |
| 1.38 | $CH_3CH=CHCH_2CH_2CH_2$ | $CH_3$ |
| 1.39 | $ClCH_2CH_2CH_2CH_2CH_2CH_2$ | $CH_3CH_2$ |
| 1.40 | $CH_3(CH_2)_7CH=CH(CH_2)_8$ | $CH_3$ |
| 1.41 | $CH_3(CH_2)_7CH=CH(CH_2)_8$ | $CH_3CH_2CH_2CH_2$ |
| 1.42 | $CH_3(CH_2)_7CH=CH(CH_2)_8$ | $CH_3(CH_2)_7CH=CH(CH_2)_8$ |
| 1.43 | Phenyl | H |
| 1.44 | Phenyl | $CH_3$ |
| 1.45 | Phenyl | Phenyl |

Suitably the invention provides the use of a compound of formula (I) in an agrochemical formulation.

Many, but not all, of the compounds used by the present invention are novel.

Therefore in a further aspect, the present invention provides a compound of formula (I) as defined above provided that when $R^1$ is $CH_3CH_2CH_2$, $(CH_3)_3C$, $(CH_3)_2CH$, $CH_3CH_2CH_2CH_2$, $(CH_3)_2CHCH_2$, $CH_3CH_2CH_2CH_2CH_2$, $CH_3CH_2CH_2CH(OH)CH_2$, $CH_3CH(CH_3)CH_2CH_2$, $CH_3CH_2CH_2CH_2CH_2CH_2$, $CH_3CH_2CH_2CH(CH_3)C(OH)$, $CH_3CH_2CH(CH_3)CH_2C(OH)$, $CH_3CH_2CH_2CH_2CH_2(CH_2CH_3)CH_2$, hexafluoroisopropyl, hydroxyisopropyl, cyclohexyl, cinacalcet, formoterol, $HOCH_2CH_2CH_2SO_3$, $CH_3CHOHCH_2SO_3$, $CH_3CH(C(CH_3)_3)CH_2CH(CH_3)CH_2$ or $CH_3CH(CH_3)CH_2CH_2C(OH)$, then $R^2$ is not the same as $R^1$; when $R^1$ is $CH_3CH(CH_3)$ then $R^2$ is not perfluorohexylethyl, perfluorooctylethyl, $(CH_3)_3C$, $CH_3CH(CH_3)CH_2$ or cyclohexyl; when $R^1$ is cyclohexyl then $R^2$ is not $CH_3CH(CH_3)CH_2$ or $(CH_3)_3C$; and when $R^1$ is hydrogen then $R^2$ is not stearyl.

The compounds of the invention may be used in a variety of applications (including agrochemical formulations), particularly as solvents. These solvents may be used with a wide variety of materials, including herbicides, fungicides, acaricides, nematicides, insecticides and plant growth regulators.

The compounds of the invention may be used to formulate solutions of a variety of materials, including agrochemicals, which may be formulated as emulsion or dispersion concentrates, emulsions in water or oil, microencapsulated formulations, aerosol sprays or fogging formulations; and these may be further formulated into granular materials or powders, for example for dry application or as water-dispersible formulations. Any solutions so formed may also be used directly on soil or plants or in other non-agrochemical applications.

Examples of suitable applications include paper making, water treatment, forestry applications, public health treatments, use in municipal pools and other water courses, in applications near rivers, lakes, reservoirs or seas and in applications where release to the atmosphere has to be minimised or controlled and where damage to the atmosphere is not desirable. Examples include use in exterior and interior paints, coatings, varnishes, waxes or other protectant layers or opacifiers, colourants or screens; in dyeing, pigmentation or the use of inks; in cleaning products designed for the home, garden or industrial applications; and in soap or detergent applications for industrial, home or environmental usage. The compounds of the present invention may also be used in shampoos, household detergency and in household cleaners [for example oven cleaners and surface cleaners].

The compounds of the present invention have exceptional dissolving power for a wide variety of agrochemicals, pharmaceuticals and other commercially valuable compounds, plus the dissolving power also extends to dissolution of dirt, grease or waxes.

The invention is illustrated by the following Examples in which:
g=grammes ° C.=degrees centigrade
N/A=not available Unless otherwise stated, each concentration is expressed as percentage by weight.

EXAMPLE 1

This Example demonstrates the low water solubility of (E)-but-2-enedioic acid di n-butyl ester. Typically, solvents which have aqueous solubilities of about (or at least) 0.1% w/w [at the relevant temperature] can dissolve appreciably in agrochemical spray tanks under normal dilution conditions [for example, temperatures of from just above freezing to 35° C.]. These solvents do not form stable emulsions in water when used by themselves. Solvents such as acetophenone are normally formulated with an oil of much lower water solubility. For example, solvents which have aqueous solubility values typically below 0.1% w/w [at the relevant temperature] are suitable for preparing emulsions. Table 2 provides water solubilities for a number of solvents at 25° C. Saturated solutions of each solvent in deionised water were prepared by leaving excess solvent in contact with water for a period of at least two weeks. After this time a sample of the water was analysed chromatographically to determine the concentration of solvent present.

TABLE 2

| Solvent | % water solubility [by weight at 25° C.] |
|---|---|
| Dodecylbenzene (1-phenyldodecane) | 0.000026 |
| Dicaprylyl carbonate (Cetiol ™ CC) | 0.000039 |
| Exxsol ™ D-80 (Dodecane) | 0.00089 |
| (E)-But-2-enedioic acid dibutyl ester | 0.04 |
| Jeffsol ™ AG-1723 | 0.04 |
| Dipentene (limonene) | 0.098 |
| Tetralin ™ (tetrahydronaphthalene) | 0.18 |
| Norpar ™ 15 | 0.4 |
| Decalin (decahydronaphthalene) | 0.7 |
| Genagen ™ 4166 (dimethyl heptamide) | 0.7 |
| Diethyl fumarate | 0.8 |
| Acetophenone (methyl phenyl ketone) | 0.9 |
| Benzyl alcohol, benzene methanol | 4.4 |
| Triacetin (glycerol triacetate) | 7.7 |

EXAMPLE 2

In this Example several solvents of the present invention were used to dissolve isopyrazam. The results show that these are effective solvents for this agrochemical. A glass vial was approximately one eighth filled with an active ingredient and then solvent was added until the vial was approximately one third full. The resultant sample was mixed with a Whirlimixer™ and was then stored at 25° C. The sample was checked every few days; if there was no solid active ingredient present then additional active ingredient was added; if there was no liquid remaining then additional solvent was added. This procedure was repeated until the sample had equilibrated for 4 weeks following the final addition of either active ingredient or solvent. The supernatant liquid layer was then analysed by gas chromotography for active ingredient concentration; the solubilities of isopyrazam in several solvents are given in Table 3:

TABLE 3

| Solvent | Isopyrazam % w/w |
|---|---|
| (E)-But-2-enedioic acid dibutyl ester | 5.0 |
| (E)-But-2-enedioic acid diisopropyl ester | 6.0 |
| (E)-But-2-enedioic acid diisobutyl ester | 4.8 |
| (E)-But-2-enedioic acid dipentyl ester | 4.6 |
| (E)-But-2-enedioic acid bis(1-methyl-butyl) ester | 3.5 |
| (E)-But-2-enedioic acid bis(3-methyl-butyl) ester | 3.7 |
| (E)-But-2-enedioic acid dihexyl ester | 3.7 |
| (E)-But-2-enedioic acid bis(2-methyl-pentyl) ester | 3.0 |
| (E)-But-2-enedioic acid bis(3-methyl-pentyl) ester | 3.1 |
| (E)-But-2-enedioic acid bis(4-methyl-pentyl) ester | 2.3 |

EXAMPLE 3

This Example shows that the solvents of the present invention are particularly effective at solubilising pesticides. Tables 4a and 4b show the solubility of the pesticides azoxystrobin, difenoconazole, isopyrazam, cyproconazole, chlorothalonil and bicyclopyrone in the solvent (E)-but-2-enedioic acid dibutyl ester. For comparison the solubilities in a series of commonly used, low water solubility solvents are also tabulated. The data show that in most cases the (E)-but-2-enedioic acid dibutyl ester was a more effective solvent. Solubilities are quoted as percentage w/w at 20° C.

TABLE 4a

| Solvent | Azoxystrobin | Cyproconazole | Difenoconazole |
|---|---|---|---|
| Dipentene | 0.14 | 1 | 5.9 |
| Norpar ™ 15 | 0.16 | 0.1 | 0.4 |
| Decalin | 0.03 | 0.4 | 1.8 |
| Exxsol ™ D-80 | 0.13 | 0.5 | 0.9 |
| Jeffsol ™ AG-1723 | 0 | 0.9 | N/A |
| Dodecylbenzene | 0 | 0.9 | N/A |
| (E)-But-2-enedioic acid dibutyl ester | 1.4 | 6.5 | 18 |
| Dicaprylyl carbonate | 0 | 2.6 | N/A |
| Tetralin | 1.85 | 5.2 | N/A |

TABLE 4b

| Solvent | Chlorothalonil | Bicyclopyrone | Isopyrazam |
|---|---|---|---|
| Dipentene | 0.18 | 7.4 | 0.8 |
| Norpar ™ 15 | N/A | 0.3 | 0.3 |
| Decalin | N/A | 1.8 | 0.3 |
| Exxsol ™ D-80 | N/A | 0.97 | 0.3 |
| Jeffsol ™ AG-1723 | N/A | N/A | 0.39 |
| Dodecylbenzene | N/A | N/A | 0.6 |
| (E)-But-2-enedioic acid dibutyl ester | 0.6 | 16 | 5.0 |
| Dicaprylyl carbonate | N/A | N/A | 1.9 |
| Tetralin | N/A | N/A | 2.6 |

EXAMPLE 4

This Example shows that (E)-but-2-enedioic acid dibutyl ester may act as an adjuvant to enhance significantly the biological performance of a pesticide. The weed species *Setaria Viridis* (SETVI), *Lolium Perenne* (LOLPE), *Avena Fatua* (AVEFA) and *Alopecurus Myosuroides* (ALOMY) were grown under glass house conditions and sprayed with the herbicide pinoxaden at a rate of 7.5 grams of pesticide per hectare. Weeds were treated with pinoxaden in the absence of (E)-but-2-enedioic acid dibutyl ester (as a control) and also with (E)-but-2-enedioic acid dibutyl ester added to the spray-tank at a concentration of 0.2% by volume. After both 14 and 21 days the efficacy of the herbicide was assessed based on the percentage of the weeds that had been killed. Three replicates were used in all cases. The average percentage of weeds killed is quoted in Table 5 for each weed species either with the adjuvant or without (control). Results have been averaged across three replicates. The standard deviation for each result is shown in brackets after the result. The results in Table 5 show that at a confidence level of 95% the solvent-containing system was found to be more efficacious than the adjuvant-free formulation.

TABLE 5

| Adjuvant | Days after application | ALOMY | AVEFA | LOLPE | SETVI |
|---|---|---|---|---|---|
| (E)-But-2-enedioic acid dibutyl ester | 14 | 20(17.3) | 20(10) | 13.3(5.8) | 20(0) |

TABLE 5-continued

| Adjuvant | Days after application | ALOMY | AVEFA | LOLPE | SETVI |
|---|---|---|---|---|---|
| None | 14 | 1.7(2.9) | 0(0) | 6.7(5.8) | 0(0) |
| (E)-But-2-enedioic acid dibutyl ester | 21 | 33.3(15.3) | 16.7(5.8) | 6.7(5.8) | 20(10) |
| None | 21 | 0(0) | 0(0) | 0(0) | 0(0) |

EXAMPLE 5

This Example shows that (E)-but-2-enedioic acid dibutyl ester can act as an adjuvant to enhance significantly the biological performance of a pesticide. The weed species *Polygonum Convolvulus, Digitaria Sanguinalis, Brachiaria Decumbens* and *Amaranthus Tuberculatus* were grown under glass house conditions and sprayed with the herbicide mesotrione at rate of 45 grams of pesticide per hectare. Weeds were treated with the mesotrione in the absence of (E)-but-2-enedioic acid dibutyl ester (as a control) and also with (E)-but-2-enedioic acid dibutyl ester added to the spray-tank at a concentration of 0.2% v/v. After 14 and 21 days the efficacy of the herbicide was assessed based on the percentage of the weeds that had been killed. Three replicates were used in all cases. The performance of the solvent was assessed by averaging the three replicates at each time period and for each weed. The standard deviation for each result is shown in brackets after the average percentage weed kill. The results in Table 6 show that at a confidence level of 95% the solvent-containing system was found to be more efficacious than the adjuvant-free formulation.

TABLE 6

| Adjuvant | Days after application | AMATU | BRADE | DIGSA | POLCO |
|---|---|---|---|---|---|
| (E)-But-2-enedioic acid dibutyl ester | 21 | 94(3.6) | 40(0) | 41.7(7.6) | 80(10) |
| None | 21 | 85(5) | 16.7(11.5) | 10(0) | 76.7(5.8) |
| (E)-But-2-enedioic acid dibutyl ester | 14 | 76.7(5.8) | 43.3(5.8) | 36.7(2.9) | 80(10) |
| None | 14 | 63.3(5.8) | 20(10) | 13.3(5.8) | 66.7(15.3) |

EXAMPLE 6

This Example describes how certain ethyl fumarates according to the present invention were prepared; for each of these fumarates, $R^1$ is ethyl; and $R^2$ is a substituted phenyl [derived from the corresponding phenol]. To a solution of the relevant phenol (3.3 mmol) in dichloromethane (2.0 ml) at 0° C. was added a solution of triethylamine (0.47 ml) in dichloromethane (2.0 ml) followed by a solution of ethyl fumaryl chloride (500 mg) in dichloromethane (2.0 ml). The reaction mixture was stirred at 0° C. until completion of the reaction and then the solvent was evaporated. The residue was partitioned between 2M $K_2CO_3$ and ethylacetate, the organics were evaporated to dryness and the crude product was purified by flash chromatography on 10 g silica cartridges using ethylacetate/hexane as eulent. Confirmation that the required ethyl fumarate had been prepared was made by NMR spectroscopy {$^1$H NMR (400 MHz, $CDCl_3$)}. The compounds tabulated, with their NMR data, in Table 7 were each prepared in this manner. In the Table, conventional terminology is used; for example, m=multiplet; s=singlet; d=doublet; dd=double doublet; t=triplet; q=quartet. Each compound of Table 7 is a compound of formula (I) where $R^1$ is ethyl and $R^2$ is as defined in Table 7.

TABLE 7

| Compound Number | $R^2$ | $^1$H NMR (400 MHz, $CDCl_3$) |
|---|---|---|
| 7.1 | 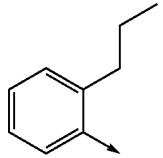 | 7.20-7.15 (4H, m), 7.05 (2H, s), 4.30 (2H, q), 2.50 (2H, t), 1.65-1.55 (2H, m), 1.35 (3H, t), 0.95 (3H, t) |
| 7.2 | 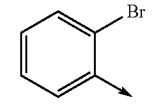 | 7.65 (1H, d), 7.35 (1H, dd), 7.20-7.10 (2H, m), 7.10 (2H, s), 4.30 (2H, q), 1.35 (3H, t) |
| 7.3 | 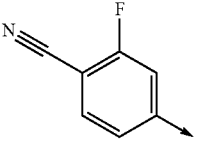 | 7.70 (1H, dd), 7.20-7.10 (2H, m), 7.05 (2H, 2 × s), 4.30 (2H, q), 1.35 (3H, t) |
| 7.4 | 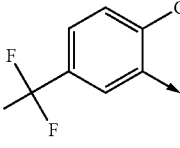 | 7.60 (1H, d), 7.50 (1H, d), 7.50 (1H, s), 7.10 (2H, s), 4.30 (2H, q), 1.35 (3H, t) |
| 7.5 | 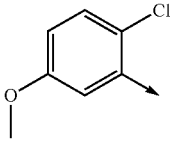 | 7.35 (1H, d), 7.05 (2H, s), 6.80 (1H, d), 6.75 (1H, s), 4.30 (2H, q), 3.80 (3H, s), 1.35 (3H, t) |
| 7.6 | 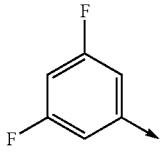 | 7.05 (2H, s), 6.80-6.70 (3H, m), 4.30 (2H, q), 1.35 (3H, t) |
| 7.7 | 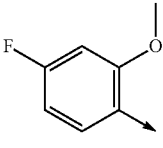 | 7.05 (2H, s), 7.05-7.00 (1H, m), 6.75-6.60 (2H, m), 4.30 (2H, q), 3.80 (3H, s), 1.35 (3H, t) |
| 7.8 | 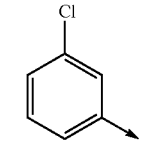 | 7.35 (1H, dd), 7.25 (1H, d), 7.20 (1H, s), 7.05 (1H, d), 7.05 (2H, s), 4.30 (2H, q), 1.35 (3H, t) |

TABLE 7-continued

| Compound Number | R² | ¹H NMR (400 MHz, CDCl₃) |
|---|---|---|
| 7.9 | 4-methoxyphenyl | 7.10 (2H, d), 7.05 (2H, s), 6.90 (2H, d), 4.30 (2H, q), 3.80 (3H, s), 1.35 (3H, t) |
| 7.10 | 3-methoxy-5-chlorophenyl | 7.00 (2H, s), 6.80 (2H, d), 6.60 (1H, s), 4.30 (2H, q), 3.80 (3H, s), 1.35 (3H, t) |
| 7.11 | 2-chloro-4-(trifluoromethyl)phenyl | 7.75 (1H, s), 7.60 (1H, d), 7.25 (1H, d), 7.10 (2H, s), 4.35 (2H, q), 1.35 (3H, t) |
| 7.12 | 2,4-dichlorophenyl | 7.50 (1H, s), 7.30 (1H, m), 7.15 (1H, d), 7.05 (2H, s), 4.30 (2H, q), 1.35 (3H, t) |
| 7.13 | 3-(trifluoromethyl)phenyl | 7.55 (2H, d), 7.45 (1H, s), 7.40-7.30 (1H, m), 7.05 (2H, s), 4.30 (2H, q), 1.35 (3H, t) |
| 7.14 | 4-(methylsulfonyl)phenyl | 8.00 (2H, d), 7.40 (2H, d), 7.05 (2H, s), 4.30 (2H, q), 3.10 (3H, s), 1.35 (3H, t) |
| 7.15 | 2-allylphenyl | 7.30-7.20 (3H, m), 7.10 (1H, d), 7.05 (2H, s), 5.95-5.85 (1H, m), 5.10-5.00 (2H, m), 4.30 (2H, q), 3.30 (2H, d), 1.35 (3H, t) |
| 7.16 | 4-chloro-2-methylphenyl | 7.25 (1H, s), 7.20 (1H, d), 7.05 (2H, s), 7.00 (1H, d), 4.30 (2H, q), 2.15 (3H, s), 1.35 (3H, t) |
| 7.17 | 3-(trifluoromethoxy)phenyl | 7.45 (1H, dd), 7.15-7.10 (2H, m), 7.10 (1H, s), 7.05 (2H, s), 4.30 (2H, q), 1.35 (3H, t) |
| 7.18 | 2,3-dichlorophenyl | 7.40 (1H, d), 7.25 (1H, dd), 7.15 (1H, d), 7.10 (2H, s), 4.30 (2H, q), 1.35 (3H, t) |
| 7.19 | 2-fluoro-3-chlorophenyl | 7.30-7.25 (1H, m), 7.20 (1H, dd), 7.10-7.05 (1H, m), 7.05 (2H, s), 4.30 (2H, q), 1.35 (3H, t) |
| 7.20 | 2,4-difluorophenyl | 7.20-7.15 (1H, m), 7.05 (2H, s), 7.00-6.85 (2H, m), 4.30 (2H, q), 1.35 (3H, t) |
| 7.21 | 3-fluorophenyl | 7.40-7.35 (1H, m), 7.05 (2H, s), 7.00-6.90 (3H, m), 4.30 (2H, q), 1.35 (3H, t) |
| 7.22 | 3-methoxyphenyl | 7.30 (1H, dd), 7.05 (2H, s), 6.80 (1H, d), 6.75 (1H, d), 6.80 (1H, s), 4.30 (2H, q), 3.80 (3H, s), 1.35 (3H, t) |
| 7.23 | 3,4-dimethylphenyl | 7.05 (2H, s), 7.00-6.90 (3H, m), 4.30 (2H, q), 2.35 (3H, s), 2.10 (3H, s), 1.35 (3H, t) |
| 7.24 | 2-cyanophenyl | 7.75-7.65 (2H, m), 7.40-7.35 (2H, m), 7.10 (2H, d), 4.30 (2H, q), 1.35 (3H, t) |
| 7.25 | 3-ethylphenyl | 7.30 (1H, dd), 7.10 (1H, d), 7.05 (2H, s), 7.00 (1H, s), 6.95 (1H, d) |
| 7.26 | 4-chloro-2-fluorophenyl | 7.25-7.10 (3H, m), 7.05 (2H, s), 4.30 (2H, q), 1.35 (3H, t) |
| 7.27 | 3-(ethoxycarbonyl)phenyl | 7.95 (1H, d), 7.80 (1H, s), 7.50 (1H, dd), 7.35 (1H, d), 7.05 (2H, s), 4.40 (2H, q), 4.30 (2H, q), 1.40 (3H, t), 1.35 (3H, t) |
| 7.28 | 4-methoxy-2-chlorophenyl | 7.10 (1H, d), 7.05 (2H, s), 7.00 (1H, s), 6.85 (2H, d), 4.30 (2H, q), 3.80 (3H, s), 1.35 (3H, t) |
| 7.29 | 4-(2-methoxyethyl)phenyl | 7.25 (2H, d), 7.05 (2H, d), 7.00 (2H, s), 4.30 (2H, q), 3.60 (2H, t), 3.35 (3H, s), 2.90 (2H, t), 1.35 (3H, t) |

The invention claimed is:

1. An agrochemical formulation comprising a herbicide, fungicide, acaricide, nematicide, insecticide or plant growth hormone dissolved in a compound of the stereoisomer of formula (I)

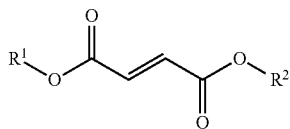

where $R^1$ and $R^2$ are each independently hydrogen, optionally substituted $C_{1-18}$ alkyl, optionally substituted $C_{1-18}$ alkenyl, optionally substituted $C_{3-8}$ cycloalkyl, optionally substituted $C_{3-8}$ cycloalkenyl or optionally substituted aryl; provided that the total number of carbon atoms in $R^1$ and $R^2$ is an integer from 5 to 40 inclusive.

2. A formulation as claimed in claim 1 where the formulation is an emulsifiable concentrate or emulsion.

3. A formulation as claimed in claim 1 provided that the total number of carbon atoms in $R^1$ and $R^2$ is an integer from 5 to 20 inclusive.

4. A formulation as claimed in claim 1 where optionally substituted aryl is substituted or unsubstituted phenyl or substituted or unsubstituted tolyl.

5. A formulation as claimed in claim 1 where $R^1$ is hydrogen or $C_{1-18}$ alkyl optionally substituted by one, two or three hydroxyl groups.

6. A formulation as claimed in claim 1 where $R^1$ is $C_{3-18}$ alkyl optionally substituted by one, two or three hydroxyl groups.

7. A formulation as claimed in claim 1 where $R^1$ is hydrogen, methyl, ethyl, linear or branched propyl, or linear or branched butyl.

8. A formulation as claimed in claim 1 where $R^2$ is propyl or butyl and $R^1$ is butyl.

9. A formulation as claimed in claim 1 where $R^1$ is hydrogen or $C_{1-2}$ alkyl and $R^2$ is substituted or unsubstituted phenyl.

10. A compound of the stereoisomer of formula (I)

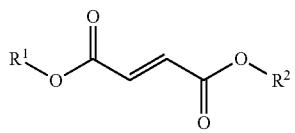

where $R^1$ and $R^2$ are each independently hydrogen, optionally substituted $C_{1-18}$ alkyl, optionally substituted $C_{1-18}$ alkenyl, optionally substituted $C_{3-8}$ cycloalkyl or optionally substituted $C_{3-8}$ cycloalkenyl; provided that the total number of carbon atoms in $R^1$ and $R^2$ is an integer from 5 to 40 inclusive; and provided that when $R^2$ is $CH_3CH_2CH_2$, $(CH_3)_3C$, $(CH_3)_2CH$, $CH_3CH_2CH_2CH_2$, $(CH_3)_2CHCH_2$, $CH_3CH_2CH_2CH_2CH_2$, $CH_3CH_2CH_2CH(OH)CH_2$, $CH_3CH(CH_3)CH_2CH_2$, $CH_3CH_2CH_2CH_2CH_2CH_2$, $CH_3CH_2CH_2CH(CH_3)C(OH)$, $CH_3CH_2CH(CH_3)CH_2C(OH)$, $CH_3CH_2CH_2CH_2CH(CH_2CH_3)CH_2$, hexafluoroisopropyl, hydroxyisopropyl, cyclohexyl, cinacalcet, formoterol, $HOCH_2CH_2CH_2SO_3$, $CH_3CHOHCH_2SO_3$, $CH_3CH(C(CH_3)_3)CH_2CH(CH_3)CH_2$ or $CH_3CH(CH_3)CH_2CH_2C(OH)$, then $R^2$ is not the same as $R^1$; when $R^1$ is $CH_3CH(CH_3)$ then $R^2$ is not perfluorohexylethyl, perfluorooctylethyl, $(CH_3)_3C$, $CH_3CH(CH_3)CH_2$ or cyclohexyl; when $R^2$ is cyclohexyl then $R^2$ is not $CH_3CH(CH_3)CH_2$ or $(CH_3)_3C$; and when $R^1$ is hydrogen then $R^2$ is not stearyl.

11. A compound of formula (I) as claimed in claim 10 provided that the total number of carbon atoms in $R^1$ and $R^2$ is an integer from 5 to 20 inclusive.

12. A compound of formula (I) as claimed in claim 10 where optionally substituted aryl is substituted or unsubstituted phenyl or substituted or unsubstituted tolyl.

13. A compound of formula (I) as claimed in claim 10 where $R^1$ is hydrogen or $C_{1-18}$ alkyl optionally substituted by one, two or three hydroxyl groups.

14. A compound of formula (I) as claimed in claim 10 where $R^2$ is $C_{3-18}$ alkyl optionally substituted by one, two or three hydroxyl groups.

15. A compound of formula (I) as claimed in claim 10 where $R^1$ is hydrogen, methyl, ethyl, linear or branched propyl, or linear or branched butyl.

16. A compound of formula (I) as claimed in claim 10 where $R^2$ is propyl or butyl and $R^1$ is butyl.

17. A compound of formula (I) as claimed in claim 10 where $R^1$ is hydrogen or $C_{1-2}$ alkyl and $R^2$ is substituted or unsubstituted phenyl.

* * * * *